United States Patent
Itoh et al.

(10) Patent No.: US 8,987,170 B2
(45) Date of Patent: Mar. 24, 2015

(54) SUCCINIMIDE COMPOUND

(71) Applicant: Sumitomo Chemical Company, Limited, Tokyo (JP)

(72) Inventors: Shigeyuki Itoh, Takarazuka (JP); Ryo Ishikawa, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/463,135

(22) Filed: Aug. 19, 2014

(65) Prior Publication Data

US 2014/0357631 A1  Dec. 4, 2014

(30) Foreign Application Priority Data

Nov. 8, 2013  (JP) .................. 2013-231814

(51) Int. Cl.
*A01N 43/84* (2006.01)
*C07D 413/02* (2006.01)

(52) U.S. Cl.
CPC ...................... *A01N 43/84* (2013.01)
USPC .......................... 504/167; 544/105

(58) Field of Classification Search
USPC .......................... 544/105; 504/167
See application file for complete search history.

(56) References Cited

U.S. PATENT DOCUMENTS 4,640,707 A  2/1987  Nagano et al.

*Primary Examiner* — Kahsay Habte
(74) *Attorney, Agent, or Firm* — Birch, Stewart, Kolasch & Birch, LLP

(57) ABSTRACT

A compound represented by formula (1):

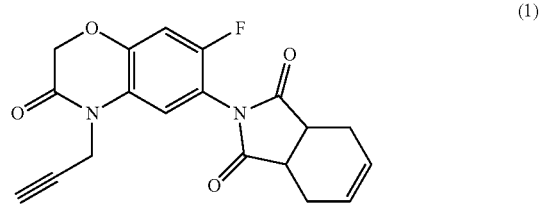

is effective for controlling *Pythium* spp., and it is useful for controlling *Pythium* spp. and protecting crops from *pythium* diseases.

3 Claims, No Drawings

SUCCINIMIDE COMPOUND

FIELD OF THE INVENTION

The present invention directs to a succinimide compound represented by the following formula (1):

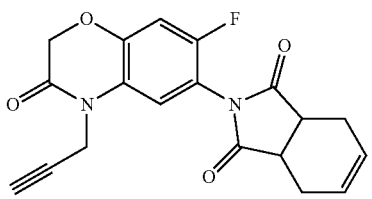
(1)

and its use for controlling *Pythium* spp.

BACKGROUND ART

A succinimide compound represented by the following formula:

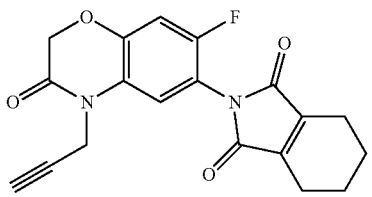 [SMILES: C#CCN1C(=O)COc2cc(F)c(N3C(=O)C4=C(CCCC4)C3=O)cc21]

is a known herbicidal compound (Flumioxazin).

SUMMARY OF THE INVENTION

The present invention provides a novel succinimide compound represented by the above formula (1), having an activity of controlling *Pythium* spp.

The compound represented by formula (1) [Compound (1)] is a compound having an effect of controlling *Pythium* spp., for example, *Pythium zingiberis* and *Pythium debaryanum*, and is useful as an active ingredient of *pythium* controlling agent.

DETAILED DESCRIPTION

The method for producing Compound (1) will be described. Compound (1) can be produced by reacting a compound represented by formula (2):

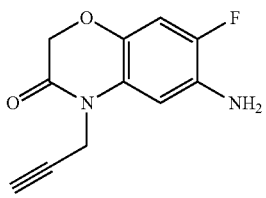
(2)

with a compound represented by formula (3):

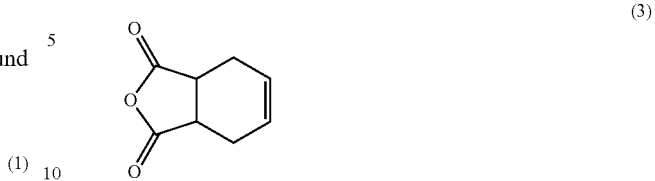
(3)

In this reaction, the amount of the compound represented by formula (3) [Compound (3)] is not particularly limited, and is preferably 0.9 to 2 equivalents and more preferably 1.0 to 1.2 equivalents, based on one equivalent of the compound represented by the formula (2) [Compound (2)].

This reaction can be carried out in an appropriate solvent. The solvent is not particularly limited as long as it does not give by-products by reacting with a reaction substrate, a reaction reagent and a product, but a solvent which sufficiently dissolves both of the reaction substrate and the reaction reagent is desirable. Examples of the solvent include aliphatic hydrocarbons such as pentane, hexane, heptane and petroleum ether; aromatic hydrocarbons such as benzene, toluene and xylene; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxides such as dimethyl sulfoxide; sulfones such as sulfolane; halogenated hydrocarbons such as dichloromethane, chloroform, 1,2-dichloroethane and carbon tetrachloride; fatty acids such as formic acid and acetic acid; and mixed solvents thereof.

The reaction temperature is usually about 50 to 200° C. and preferably about 80 to 150° C. The reaction time is generally about 0.1 to 48 hours and preferably 1 to 24 hours.

After the completion of the reaction, the reaction mixture is subjected to conventional post-treatments, for example, concentration under reduced pressure, solvent extraction, crystallization, recrystallization and chromatography, and thus the compound of the present invention can be isolated and purified.

Compound (2) can be produced according to the description of JP-A-61-140573. Compound (3) is a commercially available compound. Further, cis-form of Compound (3) that is cis-cyclohex-4-ene-dicarboxylic anhydride can be produced by a Diels-Alder reaction of maleic anhydride and butadiene.

Compound (1) is applied as it is to a place where *pythium* propagates, thereby exhibiting a control effect, but it is usually used in the form of a composition comprising Compound (1) and a carrier. The composition is usually prepared as a formulation such as emulsifiable concentrates, wettable powders, water dispersible granules, flowables, dusts or granules, by mixing Compound (1), a solid carrier and/or a liquid carrier, and adding a surfactant and other auxiliaries for formulation as necessary. In these formulations, Compound (1) is usually contained in an amount of 0.1 to 90% by weight.

Examples of the solid carrier used for formulation include fine powders or granules of minerals such as kaolin clay, attapulgite clay, bentonite, montmorillonite, acid clay, pyrophyllite, talc, diatomaceous earth and calcite, natural organic substances such as corn cob powder and walnut shell powder, synthetic organic substances such as urea, salts such as calcium carbonate and ammonium sulfate and synthetic inorganic substances such as synthetic hydrous silicon oxide.

Examples of the liquid carrier include aromatic hydrocarbons such as xylene, alkylbenzene and methylnaphthalene, alcohols such as 2-propanol, ethylene glycol, propylene glycol and ethylene glycol monoethyl ether, ketones such as acetone, cyclohexanone and isophorone, vegetable oils such as soybean oil and cottonseed oil, petroleum aliphatic hydrocarbons, esters, dimethyl sulfoxide, acetonitrile and water.

Examples of the surfactant include anionic surfactants such as alkylsulfuric acid ester salt, alkylarylsulfonic acid salt, dialkylsulfosuccinic acid salt, polyoxyethylenealkylaryletherphosphoric acid ester salt, ligninsulfonic acid salt and naphthalenesulfonate polycondensed with formaldehyde, and nonionic surfactants such as polyoxyethylenealkylaryl ether, polyoxyethylenealkylpolyoxypropylene block copolymer and sorbitanfatty acid ester.

Examples of the other auxiliaries for formulation include water-soluble polymers such as polyvinylalcohol and polyvinylpyrrolidone, gum arabic, alginic acid and salts thereof, polysaccharides such as CMC (carboxymethylcellulose) and xanthan gum, inorganic substances such as aluminum magnesium silicate and alumina sol, preservatives, colorants and PAP (isopropyl acidic phosphate), and stabilizing agents such as BHT.

*Pythium* is a genus of oomycetes, and among this genus, there is also a species causing soil-infecting diseases that give damage to crops, and it is found in soil of uncultivated land, soil of river basin or the like. The place where *Pythium* spp. to be controlled propagates may be soil of cultivated land and water source, and plant tissues of crops, flowers and the like. The plant used as a host by *Pythium* spp. may be various plants grown as crops, and for example, it is known that *Pythium zingiberis* uses plants such as ginger and Japanese ginger, and *Pythium debaryanum* uses plants such as cucumber, pea, bottle gourd and dahlia, as a host.

The composition of the present invention is applied to a plant body used as a host by *Pythium* spp., and thus *Pythium* spp. can be controlled, namely, the plant can be protected from *pythium* disease. In addition, the composition is applied to the soil in which the plant is grown or the like, and thus *Pythium* spp. in the soil can be controlled, namely, the plant grown in the soil can be protected from *pythium* disease.

When the composition is applied to foliage of a plant body, or when the composition is applied to soil, the application amount thereof can be varied with a kind of crop that is a control object plant, a kind of control object disease, an infestation level of control object disease, formulation type, application timing, weather conditions and the like, and is usually 1 to 5,000 g and preferably 5 to 1,000 g as the amount of Compound (1) per 10,000 m$^2$. Emulsifiable concentrate, wettable powder, flowable and the like are usually applied by being diluted with water and sprayed. In this case, the concentration of the compound of the present invention is usually in the range of from 0.0001 to 3% by weight and preferably from 0.0005 to 1% by weight. Dust, granule and the like are usually applied as it is without dilution.

When the composition of the present invention is applied to a plant body, it is applied to the seed of the plant, and thus the plant can be protected from *pythium* disease. Examples of the specific method thereof include a method of soaking seeds of a plant in the composition of the present invention prepared in a concentration of Compound (1) of 1 to 1,000 ppm, a method of spraying or coating seeds of a plant with the composition of the present invention prepared in a concentration of the compound of the present invention of 1 to 1,000 ppm, and a method of dust coating seeds of a plant with the composition of the present invention.

The method for controlling *Pythium* spp. of the present invention is usually performed by applying an effective amount of the composition of the present invention to a plant in which occurrence of *pythium* disease is predictable or a soil in which the plant grows. The composition of the present invention is usually used as an agricultural and horticultural fungicide, i.e., for controlling *pythium* disease on crop fields, pastures, lawn fields, tea fields, paddy fields, orchards and the like.

The composition of the present invention can also be used together with other fungicides, insecticides, acaricides, nematocides, herbicides, plant growth regulators and/or fertilizers.

EXAMPLES

Hereinafter, the present invention will be described further in detail by Examples.

The elution in column chromatography in Examples was performed under the observation by TLC (Thin Layer Chromatography). In the TLC observation, Kieselgel 60F254 (70 to 230 meshes) manufactured by Merck & Co., Inc. was adopted as a TLC plate; the solvent used as an elution solvent in column chromatography was adopted as a developing solvent; and a UV detector was adopted for detection.

Kieselgel 60 (70 to 230 meshes) manufactured by Merck & Co., Inc. was also used as silica gel for column. When a mixed solvent is used as the developing solvent, the numerical value in parentheses shows a mixing ratio of solvents by volume.

NMR spectra show proton NMR, and are determined with JEOL AVANCE 400 (400 MHz) spectrometer using tetramethylsilane as an internal standard, and all delta values are shown in ppm. The measurement temperature is 25° C. Here, the abbreviations used in the following Production Example have the following meanings:

s: singlet, brs: broad singlet, d: doublet, t: triplet, q: quartet, m: multiplet.

In addition, room temperature means about 15 to 25° C.

Production Example of the compound of the present invention is described.

Production Example 1

Synthesis of Compound of Present Invention: N-[7-fluoro-3,4-dihydro-3-oxo-4-(2-propynyl)-2H-1,4-benzoxazin-6-yl]cyclohex-4-ene-1,2-dicarboxamide

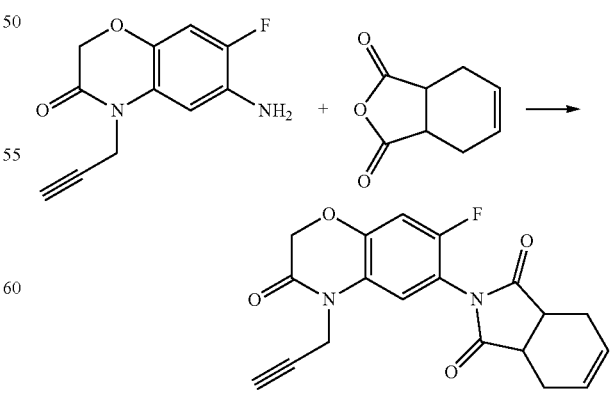

Cyclohex-4-ene-dicarboxylic acid anhydride (24.05 g) and 6-amino-7-fluoro-4-(2-propynyl)-2H-1,4-benzoxazin-3-

(4H)-one (29.01 g) were dissolved in 132 ml of acetic acid, and heated under reflux for six and half hours. The reaction mixture was added to 400 ml of water, and the precipitated crystal was collected by filtration. The resulting crystal was recrystallized from ethyl acetate to obtain N-[7-fluoro-3,4-dihydro-3-oxo-4-(2-propynyl)-2H-1,4-benzoxazin-6-yl]cyclohex-4-ene-1,2-dicarboxamide (14.31 g).

Melting point: 192 to 194° C.

$^1$H-NMR (CDCl$_3$): 2.29 (1H, t, J=2.4 Hz), 2.32-2.37 (2H, m), 2.71 (2H, d, J=15.6 Hz), 3.32 (2H, s), 4.66 (2H, d, J=2.4 Hz), 4.67 (2H, s), 6.01 (2H, t, J=2.8 Hz), 6.89 (1H, d, J=9.6 Hz), 7.00 (1H, br)

Next, Formulation Examples is shown. Here, parts represent parts by weight.

Formulation Example 1

Fifty parts of Compound (1), 3 parts of calcium lignin sulfonate, 2 parts of magnesium lauryl sulfate and 45 parts of synthetic hydrous silicon hydroxide were well pulverized and mixed to obtain a wettable powder.

Formulation Example 2

Twenty parts of Compound (1) and 1.5 parts of sorbitan trioleate were mixed with 28.5 parts of an aqueous solution including 2 parts of polyvinyl alcohol, and the mixture was finely pulverized by a wet pulverization method. Then, 40 parts of an aqueous solution including 0.05 parts of xanthan gum and 0.1 parts of aluminum magnesium silicate was added thereto, further 10 parts of propylene glycol was added, and the resultant was stirred and mixed to obtain a flowable.

Formulation Example 3

Two parts of Compound (1), 88 parts of kaolin clay and 10 parts of talc were well pulverized and mixed to obtain a dust.

Formulation Example 4

Five parts of Compound (1), 14 parts of polyoxyethylenestyrylphenyl ether, 6 parts of calcium dodecylbenzenesulfonate and 75 parts of xylene were well mixed to obtain an emulsifiable concentrate.

Formulation Example 5

Two parts of Compound (1), 1 part of synthetic hydrous silicon hydroxide, 2 parts of calcium lignin sulfonate, 30 parts of bentonite and 65 parts of kaolin clay were well pulverized and mixed, then water was added, and the resultant was well kneaded, granulated and dried to obtain a granule.

Formulation Example 6

Zero point one parts of Compound (1) and 99.9 parts of dimethyl sulfoxide were mixed to obtain a solution.

Test Example 1

Antibacterial Test on *Pythium zingiberis*

A predetermined amount of Compound (1) was dissolved in dimethyl sulfoxide, and the resulting solution was added to a potato dextrose agar medium (PDA medium) so as to have a final concentration of 500 ppm.

Separately, an agar piece containing bacteria cut out from the bacterial flora peripheral part of *Pythium zingiberis* pre-cultured in an additive-free PDA medium was inoculated on the PDA medium containing Compound (1), and cultured at 12° C. or 27° C., and then the mycelium growth inhibition rate was measured by the following Expression 1:

Mycelium growth inhibition rate(%)=100−(Diameter of bacterial flora in added medium)/(Diameter of bacterial flora in additive-free medium)×100   Expression 1

The result is shown in Table 1.

TABLE 1

| Culture temperature | Observation date | Mycelium growth inhibition rate (%) |
| --- | --- | --- |
| 27° C. | Day 1 | 53 |
| 12° C. | Day 4 | 100 |

Test Example 2

Antibacterial Test on *Pythium zingiberis*

A predetermined amount of Compound (1) was dissolved in dimethyl sulfoxide, and the resulting solution was added to a potato dextrose agar medium (PDA medium) so as to have a final concentration of 500 ppm.

Separately, an agar piece containing bacteria cut out from the bacterial flora peripheral part of *Pythium zingiberis* pre-cultured in an additive-free PDA medium was inoculated on the PDA medium containing Compound (1), and cultured at 27° C. for 4 days, and then the mycelium growth inhibition rate was measured by Expression 1.

In addition, the test was conducted in the same manner, using N-[7-fluoro-3,4-dihydro-3-oxo-4-(2-propynyl)-2H-1,4-benzoxazin-6-yl]cyclohex-1-ene-1,2-dicarboxamide as a comparative example, in place of Compound (1).

The result is shown in Table 2.

TABLE 2

| Test compound | Mycelium growth inhibition rate (%) |
| --- | --- |
| Compound (1) | 50 |
| Comparative compound | 3 |

Test Example 2

Antibacterial Test on *Pythium debaryanum*

A predetermined amount of Compound (1) was dissolved in dimethyl sulfoxide, and the resulting solution was added to a potato dextrose agar medium (PDA medium) so as to have a final concentration of predetermined concentration.

Separately, an agar piece containing bacteria cut out from the bacterial flora peripheral part of *Pythium debaryanum* pre-cultured in an additive-free PDA medium was inoculated on the PDA medium containing Compound (1), and cultured at 27° C., and then the mycelium growth state was observed. As a result, it could be confirmed that Compound (1) has an effect of controlling *Pythium debaryanum*.

INDUSTRIAL APPLICABILITY

Compound (1) is effective for controlling *Pythium* spp., and it is useful for controlling *Pythium* spp. and protecting crops from *pythium* diseases.

What is claimed is:

1. A compound represented by formula (1):

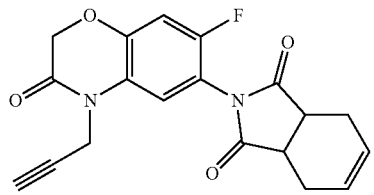

2. A composition for controlling *Pythium* spp. comprising a compound represented by formula (1):

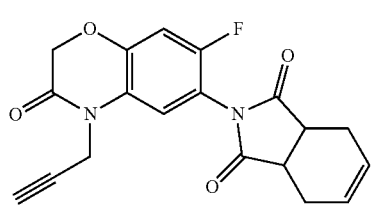

as an active ingredient and a carrier.

3. A method for controlling *Pythium* spp. wherein an effective amount of a compound represented by formula (1):

(1)

is applied to a place where *Pythium* spp. propagates.

* * * * *